BEST AVAILABLE COPY
PLT-239 SR
C5203 OR PP 003,371
July 24, 1973 S. F. HENSON Plant Pat. 3,371
AZALEA PLANT
Filed March 26, 1971
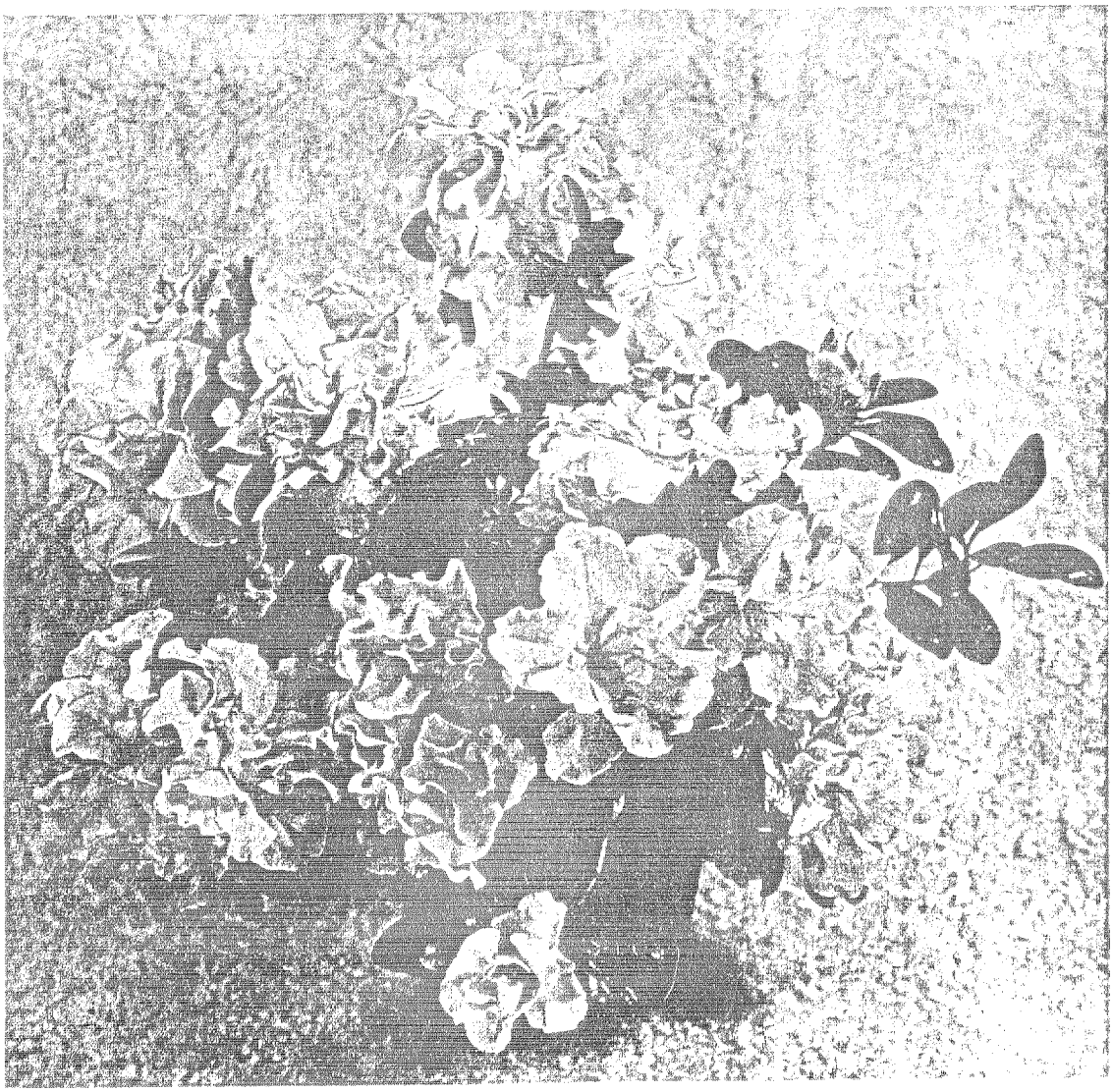

United States Patent Office

Plant Pat. 3,371
Patented July 24, 1973

3,371
AZALEA PLANT

*Stuart F. Henson, Fallbrook, Calif.*
(1053 Phillips St., Vista, Calif. 92083)

Filed Mar. 26, 1971, Ser. No. 128,595
Int. Cl. A01h *5/00*
U.S. Cl. Plt.—56 1 Claim The present invention comprises a new and distinct variety of azalea plant resulting from crossing certain azalea selections in a program controlled hybridization. The seed parent is the unpatented cultivar known as the Kurume type, Pink Pearl and the pollen parent is the unpatented cultivar Orchidflora. The new cultivar is identified by the varietal name Venus, and it is not to be confused with the southern indicum form of forcing azalea having white flowers with pink stripes, and referred to on page 249 of Lee, F. P., 1965, The Azalea Book, D. Van Nostrand Co., Inc. The cultivar referred to in the publication is not currently available commercially.

The new cultivar is similar in certain respects to the cultivar Pluto, disclosed in my copending application Ser. No. 92,331, filed Nov. 23, 1970.The cultivar Pluto is not to be confused with the evergreen variety by the same name referred to on page 249 of the above mentioned publication. The cultivar referred to in the publication has orange-red blooms, and is not currently available commercially. The new cultivar has the same characteristics as Pluto of vigorous growth and informal, horizontal growth habit. The new variety is distinguished from Pluto by the following characteristics:

1. Later budding and flowering response.
2. Larger, more double flowers, approximately one to two inches larger in diameter.
3. A more pastel pink color with a creamy colored blotch in the center of the flower and generally on the top petals of the flowers.
4. Larger foliage.

5. Heavier, stronger stems.
6. Produces fewer breaks or shoots.
7. Not recommended for year-round flowering programs, and
8. Flowering in terminal clusters thereby giving a cut flower arrangement-like effect.

The new variety was selected from a progeny of seedlings from the above mentioned parents, and was asexually reproduced by cuttings at Fallbrook, Calif. The new cultivar was found to retain its distinctive characteristics through successive propagations.

Varietal worth was determined by flowering liners from cuttings taken from the initial selection in both a year-round and natural season developmental flowering program over a period of five years. Stock growth was evaluated in the vicinity of southern Florida.

The new cultivar when grown in the vicinity of Barberton, Ohio, has a response described as late season and the following detailed description is based on observations made of the new variety in a greenhouse in Barberton, Ohio. The response time and blooming period may vary significantly with varying environmental conditions such as temperature and daylength. Suggested flowering period is from January through April in a natural season program, and the new cultivar is not recommend for year-round controlled flowering programs.

The accompanying drawing shows the unique features of my new variety, the colors being as nearly true as possible with color illustrations of this type.

The following is a detailed description of the new variety, with color references being to the Munsell Color Book, 1963 edition, and comparisons made with the cultivar Pluto. Where a characteristic or value appears only for the new cultivar, such characteristic or value applies also to the comparison cultivar Pluto. In certain instances precise color values were difficult to obtain and those values listed comprise the closest color chart values to the true color.

Botanical classification: *Rhododendron hybrida* evergreen type

| | Venus | Pluto |
|---|---|---|
| Flower: | | |
| Color, winter color in Barberton, Ohio | Light pink | Warm pink. |
| Generally tonality | Light pink, 10P8/6 | Warm pink, nearest to 5RP6/12. |
| Sepals first divide | Tip blush pink 5RP8/4 blending inwardly to dark gray pink, 5RP5/8. | Pink, 7.5RP6/12, not as gray. |
| Petals unfurl | Pink, nearest to 2.5RP7/10 but not as gray | Pink, nearest to 8.25R5/14. |
| Fully open: | | |
| Front of petals | Light lavender pink, 10P8/6 | Pink, near 5RP6/12 but not as gray. |
| Reverse side of petals | Light lavender pink, 10P8/6 but lighter | Light rose pink, near 5RP6/12 not gray, but lighter. |
| Base of petals | Light pink, 2.5RP8/6 | Blush pink, 5RP9/1 almost white. |
| Blotch | White 2.5RP9/2 with green, 2.5 GY8/6 | Deep rose pink, near 10RP4/14. |
| Discoloration as ages | Holds relative color when collapsed, light pink, 10P8/6. | Retains color for 3 weeks with gradual fading. As flowers age in a bright greenhouse, color fades to a light pink. |
| Bud: | | |
| Size | Medium | |
| Form | Conoidal | Pointed. |
| Opening habit | Fully expanded petals rosebud-like | Opens cup-like, retains cup-like form. |
| Bloom: | | |
| Size | Large | Medium. |
| Average | 4" | 2¼". |
| Range | 3"-5¼" | 1¾"-2¾". |
| Borne | Several together | Several together. |
| Average per cluster | 2.7 | 3. |
| Range of blooms per cluster | 1-4 | 1-4. |
| Form | Semi-double, occasionally double with varying degrees of petaloid anthers. | |
| Blooming habit | Once, profusely, flowers on terminal clusters giving a cut flower arrangement-like effect. | Flowers on both terminal clusters and lateral. |
| Sepals | Normal, smooth, hairy, generally persistent | |
| Calyx | Normal | |
| Peduncle: | | |
| Length | Medium | |
| Aspect | Hairy | |
| Strength | Strong | |

TABLE—Continued

Botanical classification: *Rhododendron hybrida* evergreen type

| | Venus | Pluto |
|---|---|---|
| Flower: | | |
| Petals: | | |
| Texture appearance | Soft | |
| Front of petal | Satiny | |
| Reverse side of petal | do | |
| Form | Rounded with wavy margins | Rounded with wavy margins (somewhat ruffled in appearance). |
| Arrangement | Imbricate | Imbricate with petaloids. |
| Fragrance | None | None. |
| Persistence | Shatters with age | Hang on and dry; non-shattering. |
| Longevity: | | |
| Greenhouse | 2 weeks | 3 weeks. |
| Home | 3 weeks | 4–5 weeks. |
| Reproductive organs: | | |
| Stamen | 5–10, generally petaloid | 5–10 vairable, generally petaloid. |
| Anthers | Light tan, 10YR8/4 | Light tan, 10YR8/4. |
| Filaments | Generally petaloid, light lavender pink 10P8/6 or not petaloid, thin, smooth, light pink, 7.5RP8/6. | Thin, somewhat pubescent, very light green, 2.5GY2/9. |
| Style | Columnar-normal rose pink, 7.5RP6/10 | Columnar—may be greatly reduced in size and faciated; very light green, 2.5GY2/9. |
| Stigma | Normal, light pink, near 10RP8/4 | Normal, may be fasciated; yellow green, near 5GY8/6. |
| Ovaries | Hypogynous | Hypogynous. |
| Fruit | None | None. |
| Foliage: | | |
| Type | Evergreen | Evergreen. |
| Leaflets | Single | Single. |
| Size: | | |
| Length | Average 2½″ | Average 2″. |
| Range | 1½″–3″ | 1½″–2½″. |
| Width | Average 1″ | Average ¾″. |
| Range | ½″–1¼″ | ½″–1″. |
| Shape | Obovate | Obovate to oblanceolate. |
| Texture: | | |
| Upper side | Glossy, waxy | Glossy. |
| Reverse side | Dull and smooth | Smooth. |
| Rib and mid-veins | Slightly depressed | Slightly depressed. |
| Edge | Smooth | Smooth. |
| Color—new foliage: | | |
| Upper side | Light green, 5GY4/6 | Green, near 5GY4/6. |
| Reverse side | Light green, 5GY5/6 | Green, 5GY5/4. |
| Mature foliage: | | |
| Upper side | Dark green, 7.5GY2/4 | Dark green, 7.5GY2/4. |
| Reverse side | Gray green, 5GY4/4 | Green, near 5GY5/4. |
| Petiole | Short, hairy green, 5GY6/8 | Rather long green, 5GY5/6. |
| Plant bush form: | | |
| Growth habit | Cascade, horizontal | Informal and horizontal rather than upright, but not cascading. |
| Breaking habit | Vigorous | Vigorous, informal. |
| Size of average finished product grown from the standard #7 liner of Yoder Brothers, Inc., Barberton, Ohio: | | |
| Height | 9″–10″ | 10″–12″. |
| Diameter | 12″–18″ | 12″–16″. |
| Rooting habit | Good; growth from own roots, vigorous budding ease, needs full late timing but buds well over a wide range of conditions. | Good; easy growth from own roots, vigorous, excellent uniformity of budding, growth regulator not needed for budding. |
| Growth regulator | Generally needed to develop best shaped plant | Not needed for budding. |
| Response—natural season | Late season | Early to mid-season. |
| Stems—color: | | |
| New wood | Green, 5GY6/8 | Green, 5GY7/6. |
| Mature wood | Brown, 5YR3/4 | Brown, near 10YR5/6. |
| Responsiveness to day length and temperature | Needs full timing for a late season cultivar; buds under a wide range of environmental conditions. | Buds under a wide range of conditions. |
| Shipping tolerance | Good; may bruise if shipped when flowers are fully open. | Excellent. |
| Recommended flowering period | Natural season only; January through April | Year-round; all 12 months in controlled programs. |

I claim:

1. A new and distinct variety of azalea characterized particularly as to novelty when compared to the cultivar Pluto by its large semi-double to double flowers averaging 4″ or more in diameter, a light pastel pink color with a creamy colored blotch, large glossy, waxy foliage, ability to be held for late April flowering in a natural season program, flowering in terminal clusters giving a cut flower arrangement-like effect, heavier, stronger stems, and fewer breaks or shoots.

No references cited.

ROBERT E. BAGWILL, Primary Examiner